United States Patent [19]
Pethig et al.

[11] Patent Number: 5,795,457
[45] Date of Patent: Aug. 18, 1998

[54] MANIPULATION OF SOLID, SEMI-SOLID OR LIQUID MATERIALS

[75] Inventors: Ronald Pethig, Anglesey; Julian Paul Hillhouse Burt, Bangor, both of Wales

[73] Assignee: British Technology Group Ltd., London, England

[21] Appl. No.: 461,070

[22] Filed: Jun. 5, 1995

Related U.S. Application Data

[63] Continuation of Ser. No. 952,456, Jul. 29, 1992, abandoned which is a continuation of PCT/GB91/00122, Jan. 29, 1991.

[30] Foreign Application Priority Data

Jan. 30, 1990 [GB] United Kingdom ............... 9002092

[51] Int. Cl.$^6$ ............................................................. C25B 7/00
[52] U.S. Cl. ........................... 204/547; 204/554; 204/643; 204/660
[58] Field of Search ................................. 204/547, 554, 204/643, 660

[56] References Cited

U.S. PATENT DOCUMENTS

| | | | |
|---|---|---|---|
| 3,162,592 | 12/1964 | Pohl | 204/183.1 |
| 3,197,393 | 7/1965 | McEue | 204/183.1 |
| 3,687,834 | 8/1972 | Candor | 204/183.1 |
| 3,893,898 | 7/1975 | Candor | 204/180 R |
| 4,326,934 | 4/1982 | Pohl | 204/180 R |
| 4,390,403 | 6/1983 | Batchelder | 204/180 R |
| 4,441,972 | 4/1984 | Pohl | 204/180 R |
| 5,126,022 | 6/1992 | Soane et al. | 204/180.1 |
| 5,344,535 | 9/1994 | Betts et al. | 204/183.1 |
| 5,589,047 | 12/1996 | Coster et al. | 204/450 |
| 5,626,734 | 5/1997 | Docoslis et al. | 204/547 |

FOREIGN PATENT DOCUMENTS

WO 91/11262  8/1991  WIPO .

OTHER PUBLICATIONS

Adamson et al., "An Automated Stream Centred Dielectrophoretic System", *IEEE Industry Applications Society Annual Meeting*, Part II, 1986, pp. 1350–1354.

Burt et al., "An optical dielectrophoresis spectrometer for . . . suspensions", *Journal of Physics E: Scientific Instruments*, vol. 22, Nov. 1989, pp. 952–957.

Price et al., "Applications of a new optical technique for measuring . . . micro–organisms", *Biochimica et Biophysica Acta* 964, 1988, pp. 221–230.

Masuda et al., "Movement of Blood Cells in Liquid by Nonuniform Traveling Field", *IEEE Transactions on Industry Applications*, vol. 24, No. 2, Mar./Apr. 1988, pp. 217–221.

Arnold et al., "Electric Field–Induced Fusion and Rotation of Cells", *Biological Membranes*, vol. 5, 1984, pp. 390–455.

H.A. Pohl, "Dielectrophoresis — The behavior of neutral matter in nonuniform electric fields", *Cambridge University Press*, 1978.

R. Pethig, "Dielectric and Electronic Properties of Biological Materials", John Wiley & Sons, 1979, pp. 186–207.

*Primary Examiner*—Cecilia J. Tsang
*Assistant Examiner*—C. Delacroix-Muirheid
*Attorney, Agent, or Firm*—Cushman Darby & Cushman IP Group of Pillsbury Madison & Sutro LLP

[57] ABSTRACT

By applying two or more electrical fields (DC, AC, pulsed) of different characteristics to an electrode array on e.g. the wall of a treatment cell, particles suspended in liquid in the cell may be manipulated as desired on a microscopic scale, in particular by exploiting the dielectrophoretic properties of the particles. The particles may be solid, semi-solid or liquid, and may be of simple materials or may be biological particles such as whole cells or fragments thereof.

22 Claims, 12 Drawing Sheets

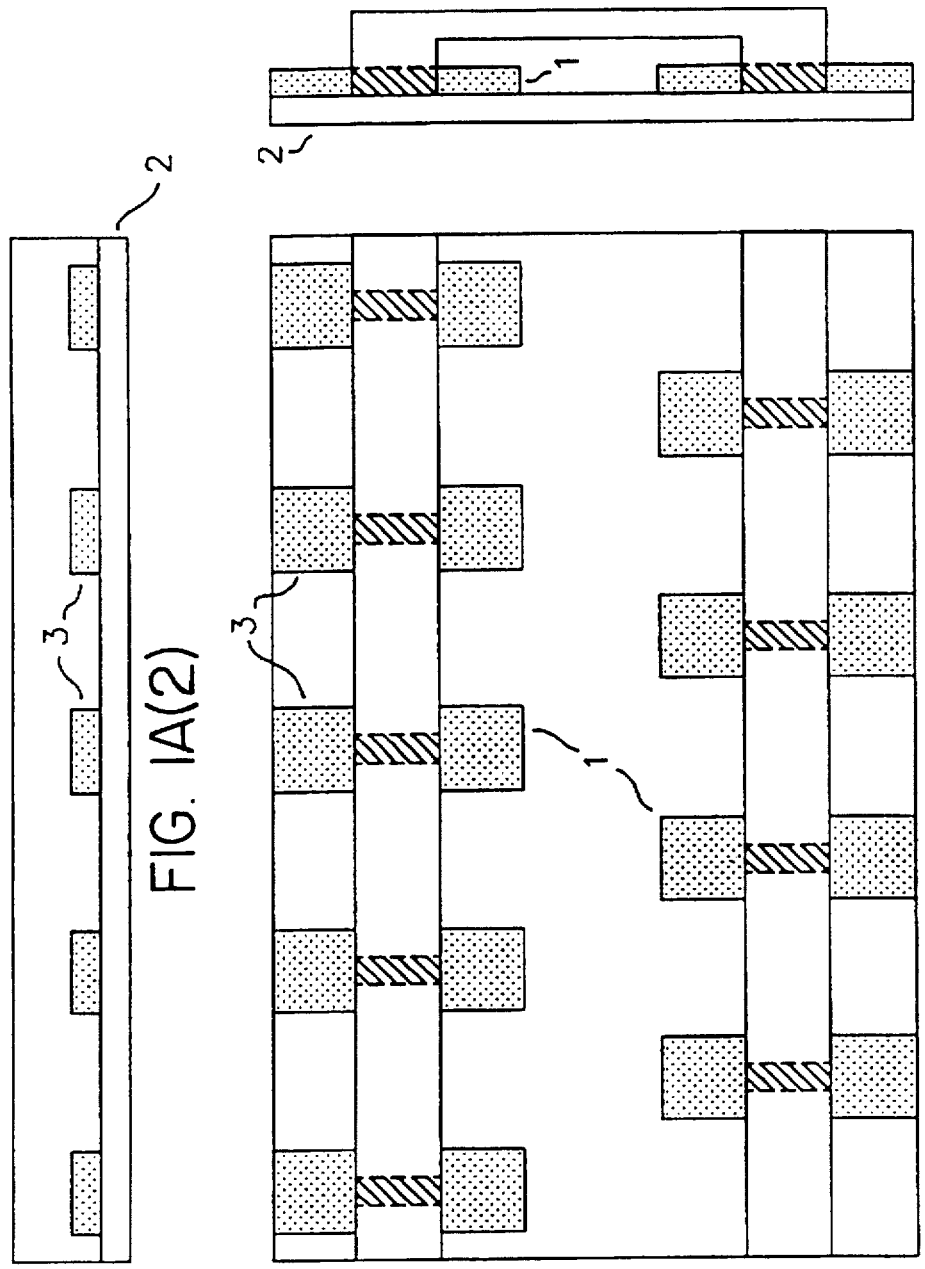
FIG. 1A(1)
FIG. 1A(2)
FIG. 1A(3)

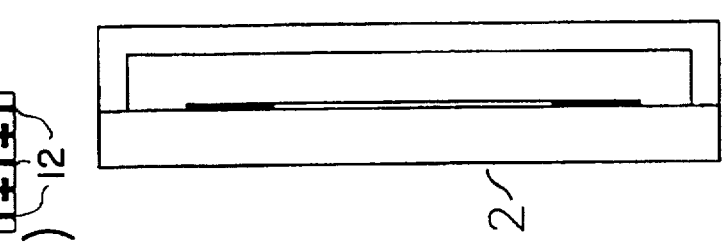
FIG. 1B(1)(a)
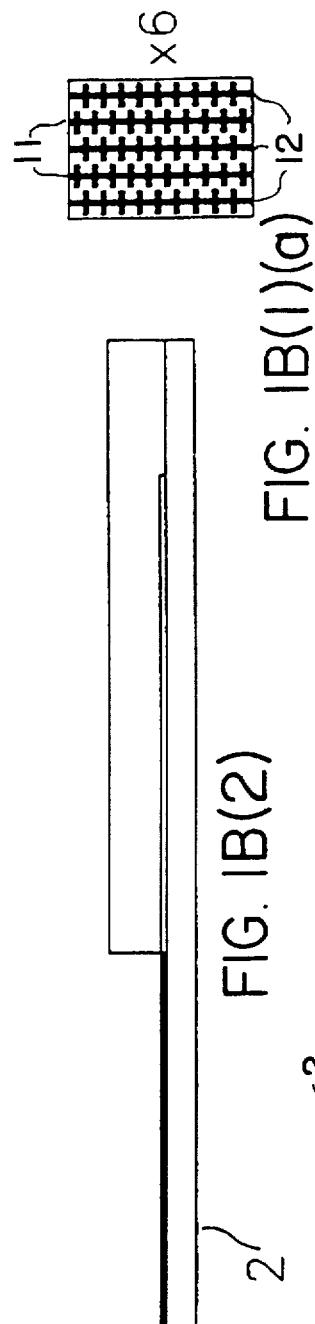
FIG. 1B(2)
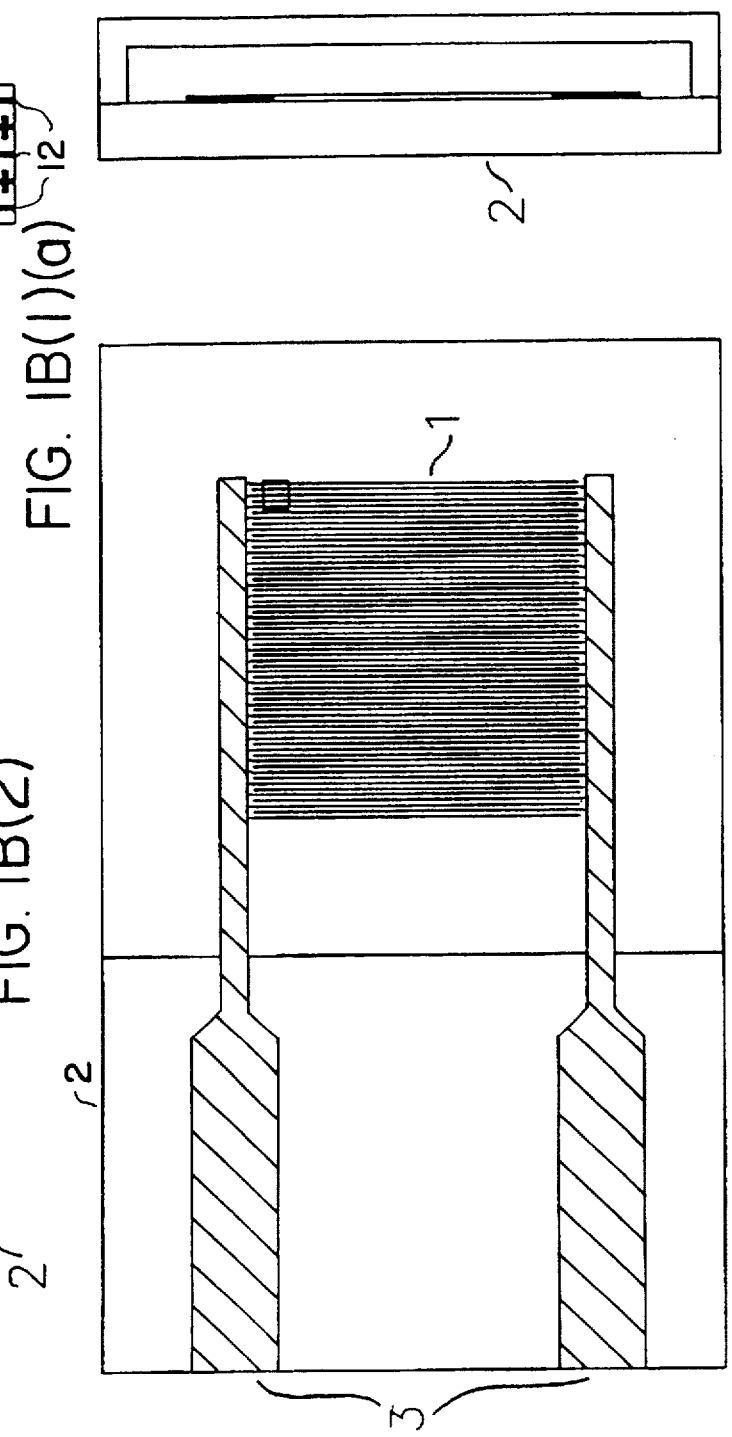
FIG. 1B(1)
FIG. 1B(3)

MANIPULATION OF SOLID, SEMI-SOLID OR LIQUID MATERIALS

This is a continuation of application Ser. No. 7/952,456, filed Jul. 29, 1992, now abandoned, which is a continuation of PCT/GB91/00122, Jan. 29, 1991.

BACKGROUND OF THE INVENTION

This invention relates to the manipulation of solid, semi-solid or liquid materials in liquid media.

A wide variety of commercial processes involve the use of liquid media having solid, semi-solid or liquid particles suspended in them. The particles may vary very widely from inert inorganic materials through to reactive materials, and organic or biological structures such as cells or parts of cells.

It has been known for some time that particles of these various types may be caused to move within a liquid medium by the use of a non-uniform electric field, and the basic phenomenon of dielectrophoresis has been extensively discussed, for example see "Dielectrophoresis", Cambridge University Press, 1978 by H. A. Pohl and Chapter 6 of "Dielectric and Electronic Properties of Biological Materials", John Wiley & Sons 1979 by Ronald Pethig.

Recently the application of dielectrophoresis has been suggested in the area of materials classification: the construction of a so-called "optical dielectrophoresis spectrometer" is described in Burt, Al-Ameen & Pethig, "An optical dielectrophoresis spectrometer for low-frequency measurements on colloidal suspensions", Journal of Physics, Section E, Scientific Instrumentation, Volume 22 (1989) pages 952 to 957.

That paper, and the related paper "Applications of a New optical Technique for Measuring the Dielectrophoretic Behaviour of Microorganisms", Price, Burt and Pethig Biochimica et Biophysica Acta 964 (1988) pages 221 to 230, disclose the use of interdigitated electrodes deposited on a dielectric substrate to cause movement of suspended particulates by the dielectrophoretic effect.

SUMMARY OF THE INVENTION

Most previous work has been directed to the characterization of materials by taking appropriate measurements of their electric field-induced properties. Another major application is the use of positive dielectrophoretic forces to align biological cells between electrodes prior to their electrofusion, as described by W. M. Arnold and U. Zimmermann ("Electric Field Induced Fusion and Rotation of Cells", Biological Membranes 5, 389–454, 1984). Also, a method and apparatus for dielectrophoretic manipulation of chemical species has been described by J. S. Batchelder (U.S. Pat. 4,390,403, Jun. 28, 1983). This method employs DC non-uniform electrical fields to manipulate one or more chemicals within a multi-electrode chamber so as to promote chemical reactions between the chemical species. The applied voltage may be periodically reversed in sign to decrease ionic shielding effects (see column 3, line 62 to column 4, line 3). The manipulation of the chemicals is controlled by positive dielectrophoretic forces resulting from differences in the dielectric constants of the chemical species.

In previous works of S. Masuda, M. Washizu and I. Kawabata "Movement of Blood Cells in Liquid by Nonuniform Travelling Field", IEEE Transactions on Industry Applications, Volume 24 (1988) pages 217 to 222, blood cells were caused to move under the influence of a non-uniform travelling electric field. This field was generated by applying two, fixed-frequency, multiphased, voltage signals, related by having the same frequency and amplitude, to a series of parallel electrodes. Likewise, the rotating electric field described by W. M. Arnold and U. Zimmermann and employed to cause rotation of a single cell, is generated using either a single, phase-split, voltage signal or synchronized, identical, voltage pulses. The present invention utilizes two or more electric fields that are generated using electrically independent voltages that do not share the same frequency of oscillation.

We have now found that if two or more non-uniform electric fields of differing frequencies are imposed, simultaneously or sequentially, on a suspension of particles of one or more than one type in a liquid, using appropriate electronic control, various reactions may be stimulated to occur in the particles in the liquid.

Thus, in accordance with a first broad aspect of the invention, a method of promoting reactions between particles suspended in a liquid is provided, the particles being of uniform type. The method, comprises applying two or more independent non-uniform electrical fields of different frequencies to the liquid from an electrode array in such a fashion as to provoke or promote the desired reaction.

The term reaction as used herein is to be interpreted broadly as covering various chemical, biochemical and physical interactions, and large scale manipulations such as separation followed by recombination, optionally with a treatment being selectively applied to one component of a multicomponent system while so separated from the other component(s).

Whereas previous work (e.g. Batchelder) has employed differences in the dielectric constant of the manipulated chemical species to control the desired reactions, we have found that, in addition to varying the dielectric constant, varying the electrical conductivity of either or both the suspended particles and the suspending medium provides a further degree of control. In this connection (and throughout this specification) the term dielectric constant is used to refer to the real part of the complex permittivity.

The particles which may be used may be of animate or inanimate material and they may be colloidal or of some other nature.

With appropriate choice of the dielectric constant and electrical conductivity of either or both the suspended particle and suspending medium, both positive and negative dielectrophoretic forces may be employed as the manipulating agent. Preferably, in carrying out the method of the invention, at least one of the electrical fields is chosen to effect a negative dielectrophoretic force on some only of the particles in the liquid. By appropriate choice of electrode geometry, it is possible to achieve at appropriate regions within the electrode geometry, regions where particular species of particle segregate or particular particle agglomerations occur. In order to enable adequate quantities of suspension to be treated, the electrodes may take the form of a repeating pattern array, or. e.g. two electrodes may be comblike and inter-engaged with each extending part of each lying between two neighboring such parts of the other.

The present invention also provides apparatus for carrying out the method of the invention including a treatment cell including an electrode array, means for feeding a suspension of particles in a liquid to the treatment cell, and means for removing liquid from the cell. First means connected to electrodes in the cell are adapted to generate a first non-uniform electrical field within the cell, and second means connected to electrodes in the cell and adapted to generate a second non-uniform electrical field within the cell having a frequency which differs from that of the non-uniform first electrical field.

Preferably, the electrode array is mounted on en external wall of the treatment cell. Such an arrangement preferably includes, as part of the liquid removing means, perforations in the external wall of the cell bearing the electrodes, the perforations being so located that, when the electrodes are appropriately electrically activated relative to the particles in the liquid medium in the cell and to the liquid medium itself, the liquid and particles drawn off through the perforations will differ from the general bulk characteristics of the suspension of particles in the liquid in the cell.

In the description of specific illustrated apparatus which follows, for simplicity of expression, reference is made to applying signals to electrodes. It should be understood that in order to create the appropriate electric fields, the signal is, in practice, applied across a pair of electrodes, one of which may be a reference electrode or an extensive surface area 'ground plate' or the like.

Depending upon the nature of the particles in the suspension, the nature of the suspension itself, and the nature of the applied electrical fields to the electrode array, the particles may be caused to aggregate towards regions of an electrode or a number of electrodes or alternatively detach themselves from such electrode(s) and/or aggregate towards regions away from the electrodes. These phenomena may be exploited in a wide variety of applications to manipulate the particles in suspension, e.g. to provide the directed assembly of structures from such suspended particles, or to provide separation from a mixture of suspended particles of different types, to provide characterization of particular particle types or to promote a reaction between particles of two or more different types.

BRIEF DESCRIPTION OF THE DRAWINGS

The accompanying drawings will serve to illustrate the invention in more detail by way of example. In the drawings:

FIGS. 1A(1)–1A(3) and 1B(1)–1B(3) and 1B(1)(a) show top, side and end views of two different examples of electrode geometries which may be used in the method of the present invention.

FIGS. 1A(1)–1A (3).

DESCRIPTION OF THE PREFERRED EMBODIMENTS

Figure 2:
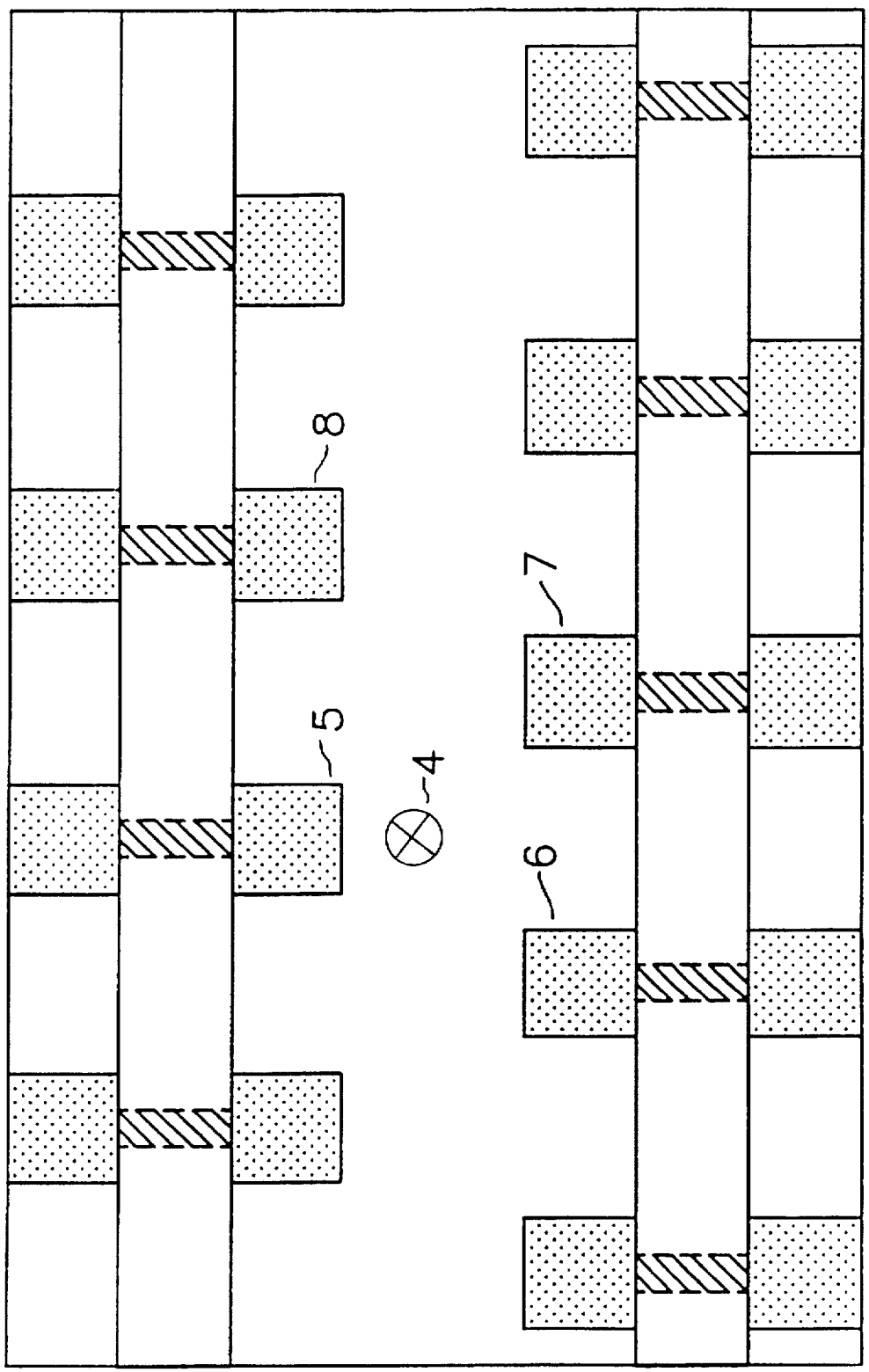
FIGS. 2 and 3 show diagrammatically the movement of a particle using the electrode array of FIG.

Referring to the drawings, FIG. 1A(1)–1A(3) show in plan, side and end views, respectively, one wall of a treatment cell which can be used to manipulate a suspension consisting of one or more particle types. The apparatus comprises an array of electrodes 1 fabricated on a suitable substrate 2 that forms the wall or surface of the treatment cell. Each electrode can be individually and independently energized by any form of electrical signal via electrical connectors 3. The electrodes 1 may be in direct electrical contact with the particle suspending liquid or separated from it by an appropriate material. For the purpose of illustration the electrodes 1 in FIG. 1A(1)–1A(3) are shown having a rectangular geometry, but other geometries may be used depending on the particle characteristics and the desired effect to be achieved.

FIG. 2 shows the array of electrodes 5–8 and a test particle 4 suspended in a liquid adjacent to the array of electrodes 5–8. By applying an appropriate electrical signal to electrode 5, the test particle 4 can be dielectrophoretically attracted towards electrode 5. This effect is enhanced by applying, at the same time, another electrical signal to electrodes 6 and 7 such that test particle 4 is dielectrophoretically repelled from electrodes 6 and 7. The electrical signals are applied to electrodes 5, 6 and 7 until test particle 4 becomes immobilized at electrode 5 or reaches a desired locality in the region of electrode 5. The particle can then be further moved by applying, for example, electrical signals which repel the particle from the region of electrode 5 and attract it towards electrode 8.

Figure 3:
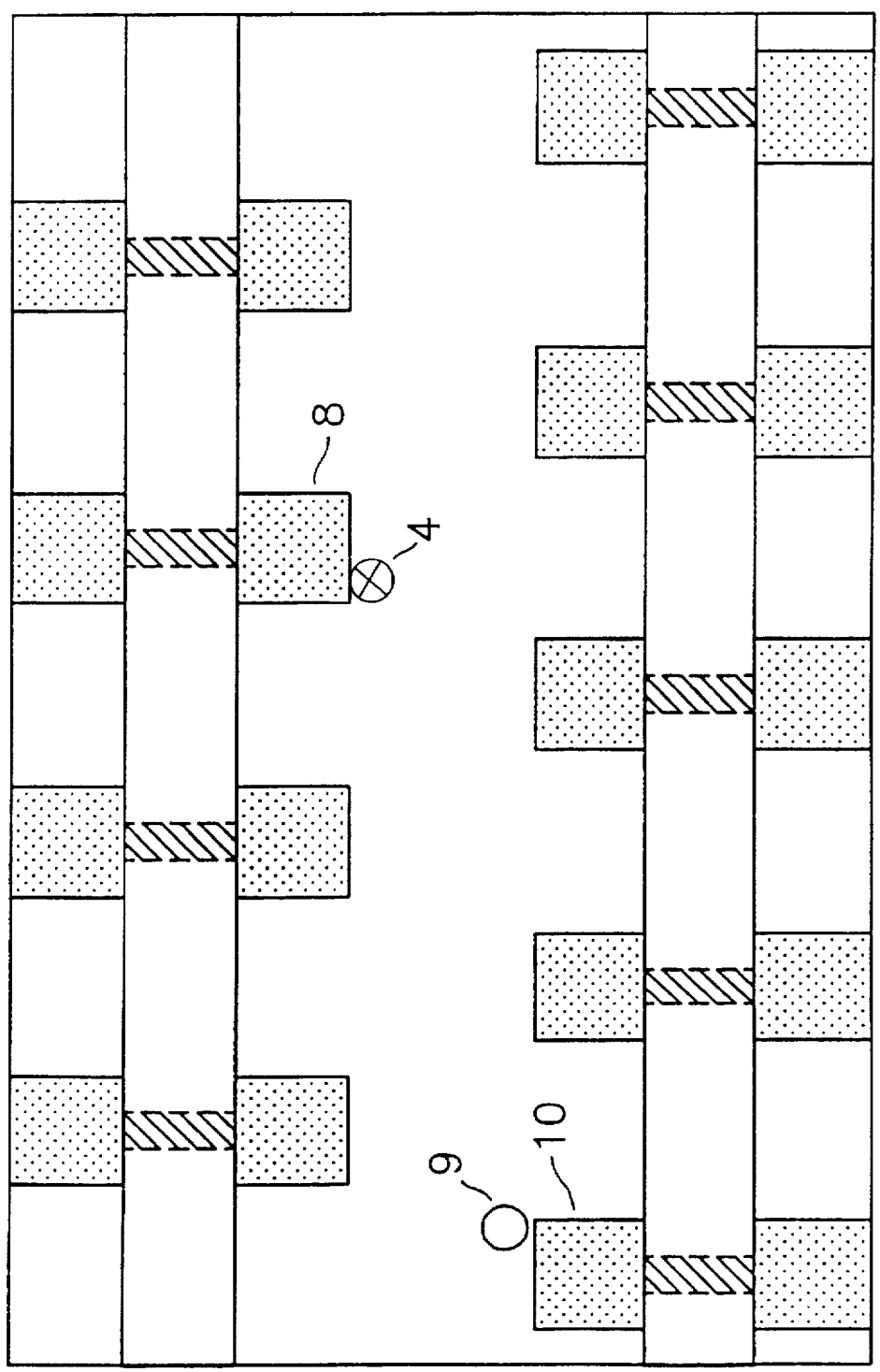

FIG. 3 shows particle 4 after it has been dielectrophoretically manipulated to the region of electrode 8 and also shows another particle 9 located at an electrode 10. Particle 9 may or may not have the same dielectric and conductive properties as particle 4. Particles 4 and 9 may be positioned alongside each other by dielectrophoretically moving either or both of them. Bringing particles 4 and 9 (and any others in like fashion) into association may be effected for the purpose of constructing larger building blocks or for inducing a specific chemical, biological or electrochemical reaction between them. This example describes the bringing together of particles but, in the more general case, the apparatus may be employed to manipulate particles into any desired positions relative to each other.

Figure 4:
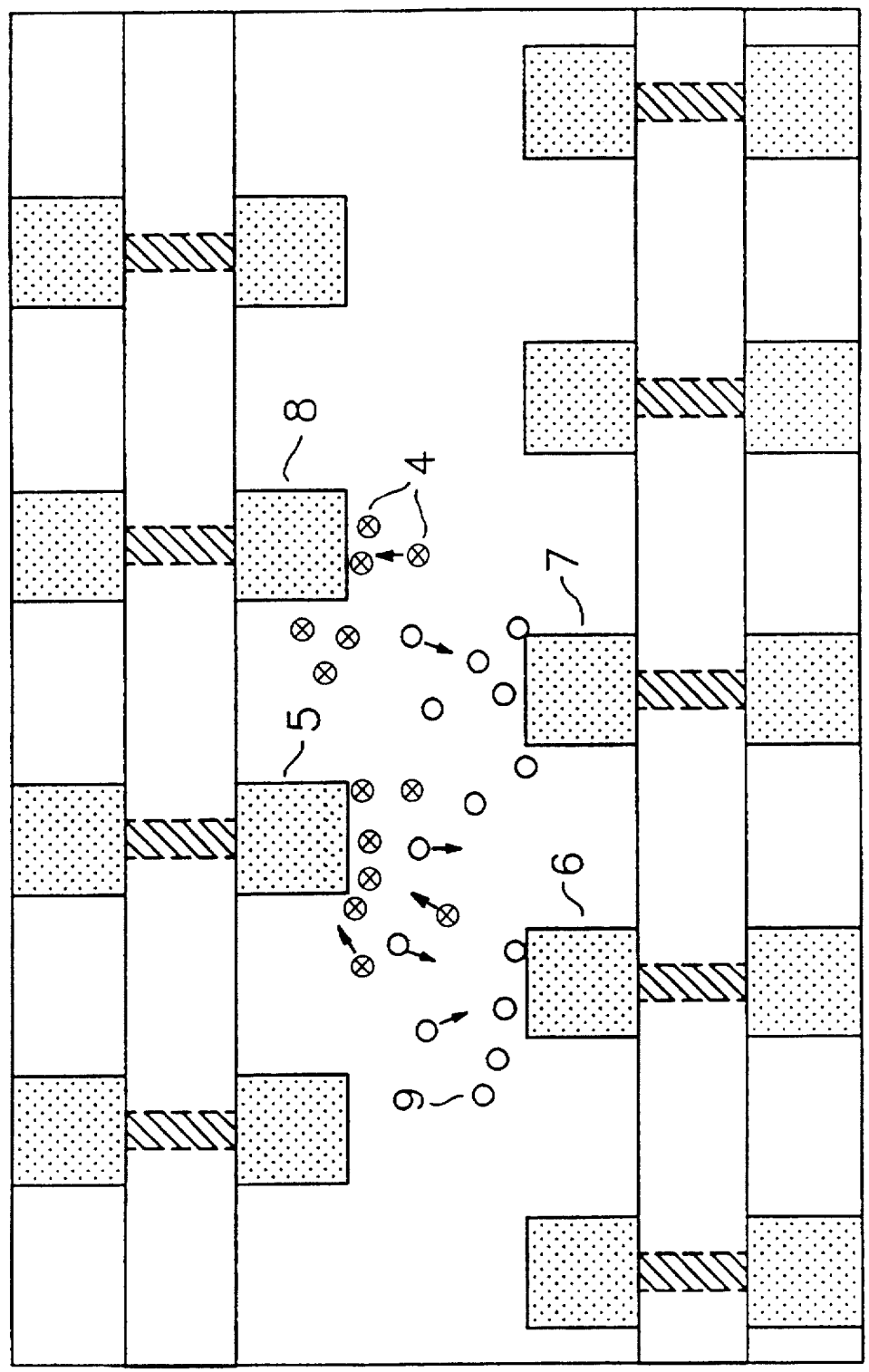
FIG. 4 shows diagrammatically a more complex situation.

FIG. 4 shows a collection of particles composed of particle types 4 and 9, which in this case possess differing bulk and/or surface electrical properties. By applying an electrical signal to electrodes 5 and 8 that differs from the signal applied to electrodes 6 and 7, and by an appropriate choice of signal characteristics (i.e. waveform, magnitude and frequency) as well as the suspending medium characteristics (e.g. pH, dielectric constant, conductivity and specific density) particle types 4 and 9 may be physically separated from each other with, for example, particle type 4 collecting near electrodes 5 and 8 and particle type 9 collecting near electrodes 6 and 7. The electrical signals applied to electrode pairs 5 and 8 and 6 and 7, or any other electrode combination, may be applied continuously or intermittently, and at the same or differing times, in order to achieve the desired separation. The particle types may then be removed separately from the treatment cell by drawing off the particle suspending fluid through perforations located near the electrodes, having first released the desired particle type from the electrodes either by removing the electrical signal used to collect them or, if strong electrode adhesion occurs, releasing them by applying electrical signals of appropriate characteristics to the electrodes. The extent of particle collection at the electrodes can be continuously assessed using an optical monitoring technique as described by Burt, Al-Ameen and Pethig in the Journal of Physics, Section E. Scientific Instrumentation. Volume 22 (1989) pages 952 to 957, and the subsequent release of particles can likewise be monitored by an optical probe at the electrodes and also downstream of the perforations.

FIG. 1B(1)–1B(3) shows, in plan, side and end views, respectively, another electrode geometry which can be used to manipulate a suspension consisting of one or more particle types. For the purpose of illustration, the electrodes 11, 12 in FIG. 1B(1)–1B(3) are shown having a castellated, interdigitated, rectangular, geometry, but other geometries may be used depending on the particle characteristics and the desired effect to be achieved.

Figure 5A:
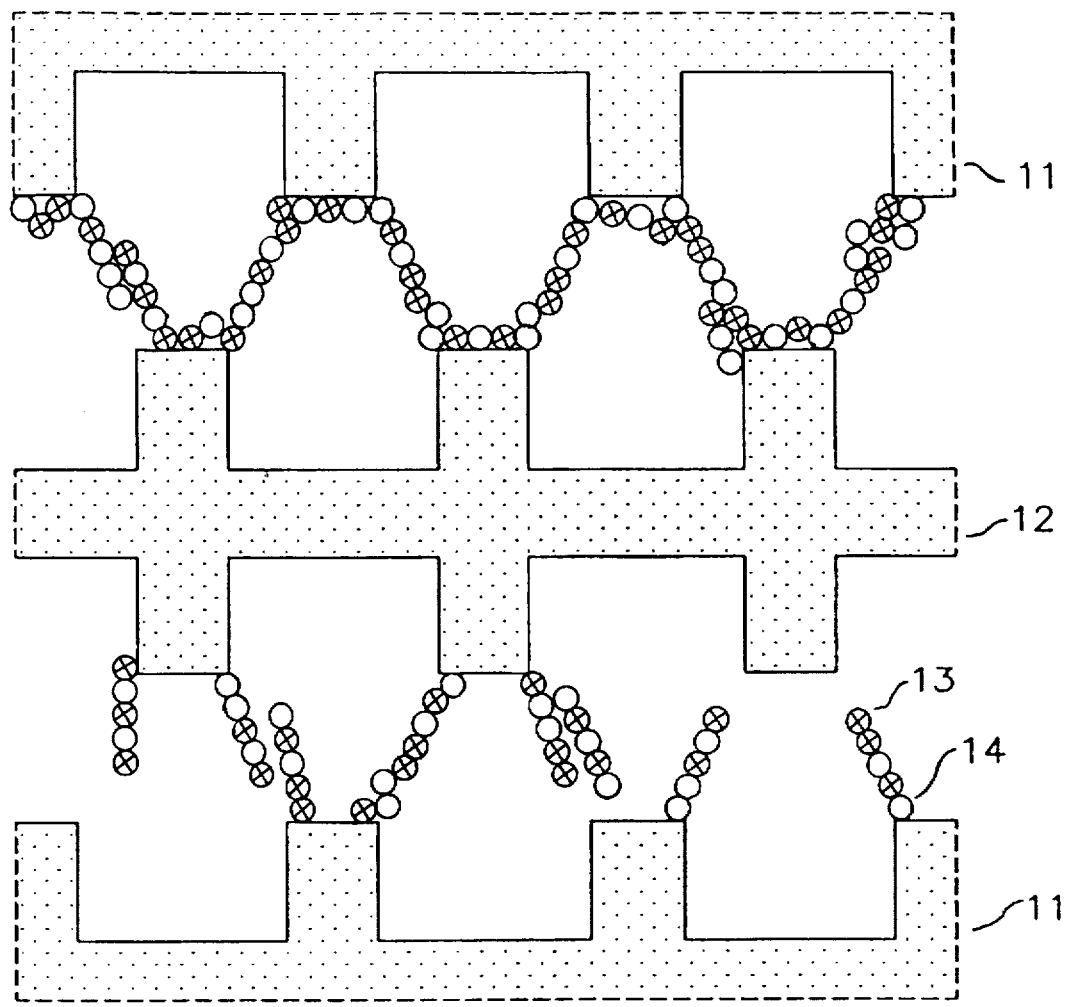
FIGS. 5A, 5B and 5C show the electrode geometry of FIG. 1B(1)–1B(3) and examples of particle aggregation at regions on the electrodes and regions away from the electrodes.

FIG. 5A shows diagrammatically a section of an array of interdigitated, castellated, electrodes 11 and 12 after the application of a voltage between electrodes 11 and 12. Two different particle types 13 and 14 have been aggregated as long chains at the outer tips of the individual electrode castellations, as a result of both particle types experiencing a positive dielectrophoretic force.

Figure 5B:
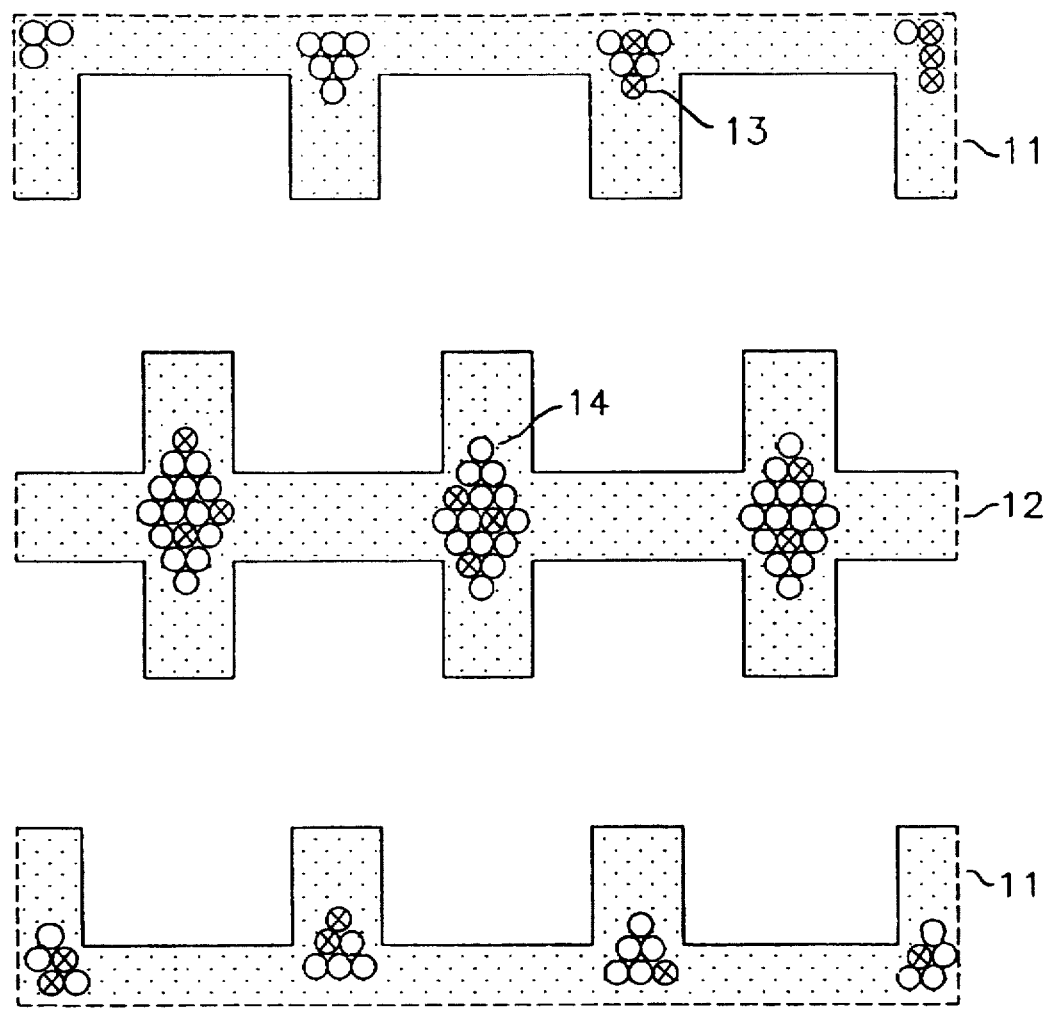

FIG. 5B shows diagrammatically the same type of electrode configuration as in FIG. 5A, where two different particle types 13 and 14 have been aggregated into regions of the upper electrode surfaces, away from the electrode sides, as a result of experiencing a negative dielectrophoretic force.

Figure 5C:
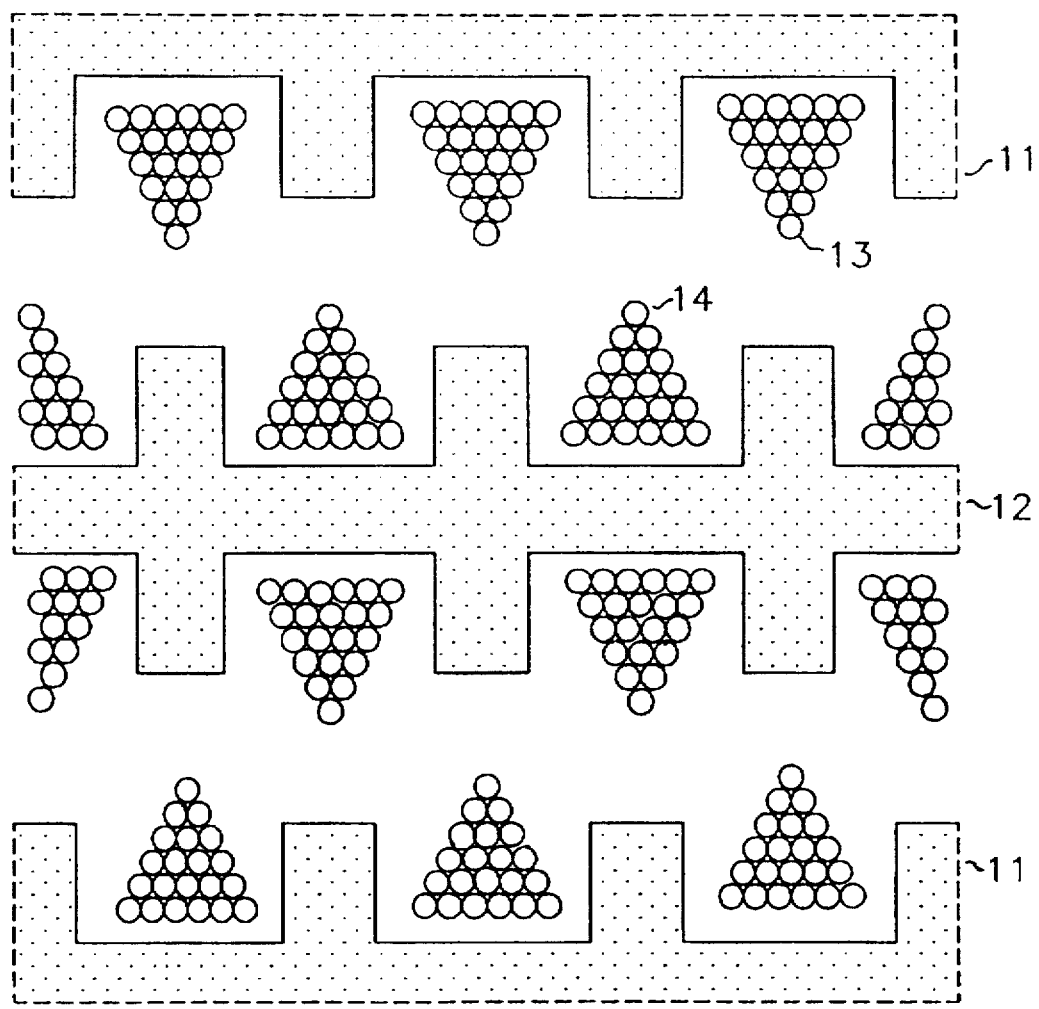

FIG. 5C shows diagrammatically the same type of electrode configuration as in FIGS. 5A and 5B, where two different particle types 13 and 14 have been directed into forming triangular-shaped aggregations in the regions between the electrode castellations away from the electrode sides, as a result of experiencing a negative dielectrophoretic force.

The following Examples will serve to illustrate the invention.

EXAMPLE 1

A cell was taken with an array of interdigitated, castellated, electrodes substantially as shown in FIGS. 1B(1)–1B(3). Each castellation was 20 microns wide, 40 microns deep, about 0.1 micron high, spaced at 80 micron centers, the interdigitated electrode rows being 80 microns apart. The entire array had sixty electrodes in each row, and was around 5mm long. The array was located on one wall of a cell having 7.5 cubic mm of internal volume.

A suspension in a medium of 280 mM mannitol in deionized water containing as suspended particles *Micrococcus lysodeikticus* (ellipsoids around 2 microns long and 0.5 microns across) was added in equal amount to a suspension of latex particles (1.27 micron diameter) in deionized water. The concentration of suspended particles was such that the optical absorbance at a wavelength of 635 nm, and 1 cm path length, was, in each case, 1.61 (cf deionized water). The conductivity of the Micrococcus suspension was 11.4 micro-Siemens per cm, whilst that of the latex particle suspension was 2.1 micro-Siemens per cm. When evenly distributed, the amount of interaction between the latex particles and the Micrococcus was very small.

On application of a voltage of 4 V p/p sinewave at a frequency of 100 kHz, the latex and Micrococcus, particles aggregated as long chains at the outer tips of the individual electrode castellations in a similar manner to that shown in FIG. 3 of the 1988 Biochimica et Biophysica Acta paper of Price, Burt and Pethig, and as also schematically shown in FIG. 5A. The term "positive dielectrophoresis" as used herein is to be interpreted broadly as this form of particle aggregation in which the particles move towards the areas of higher field strength. On removal of the applied voltage, the latex and Micrococcus particles separated from each other and became dispersed in the suspending medium. This process of bringing the latex and Micrococcus particles into intimate contact with each other, and then letting them separate, can be repeated many times.

On application of a voltage of 4 V p/p sinewave at a frequency in the range between 100 Hz and 1 kHz, the latex and Micrococcus particles aggregated at regions of the upper electrode surfaces, away from the electrode sides, as illustrated in FIG. 5B. This form of particle aggregation, where the particles are directed away from high electric field regions at electrode edges, is not the normal form of positive dielectrophoresis, and herein is to be interpreted broadly as negative dielectrophoresis.

EXAMPLE 2

A cell was taken of the same form as that in Example 1, but each electrode castellation was 80 microns wide, 80 microns deep, about 0.1 micron high, spaced at 160 micron centers and with the interdigitated electrode rows being spaced at 160 microns apart. The entire electrode array had sixty electrodes in each row, and was around 1.0 cm long. The array was located on one wall having an a cell of internal of 30 cubic mm.

A suspension in a medium of 280 mM mannitol in deionized water was prepared containing as suspended particles equal numbers of live Brewers yeast cells and dead (autoclaved) Brewers yeast cells to an optical absorbance of about 0.8 at a wavelength of 635 nm for 1 cm path length. On application of a voltage of 20 V p/p sinewave at a frequency range of 100 Hz to 20 MHz, both the live and dead yeast cells experienced a positive dielectrophoretic force and collected at the outer tips of the electrode castellations.

Figure 6:
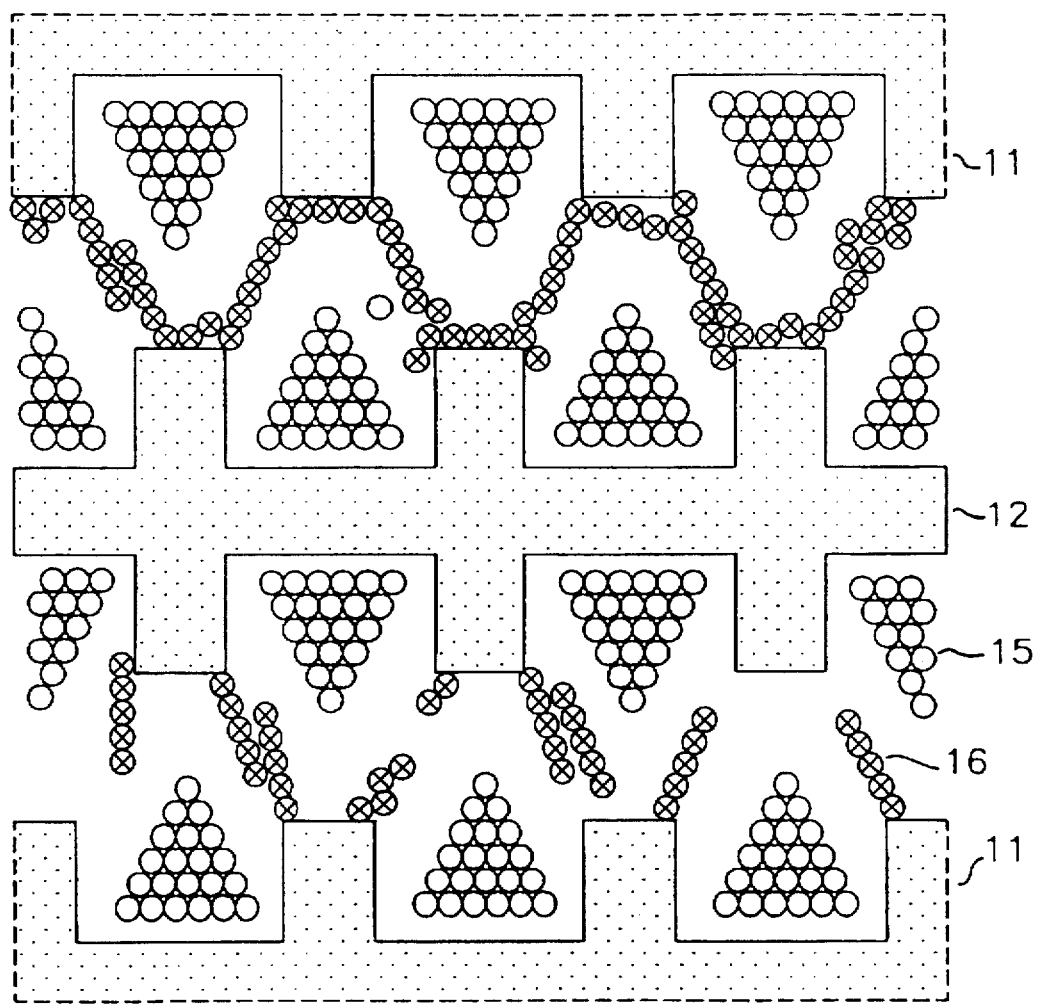
FIG. 6 shows diagrammatically two different particle types collected at the same time using both positive and negative dielectrophoretic forces.

On increasing the electrical conductivity of the mannitol suspending medium, by the addition of potassium chloride, to a conductivity of 150 micro-Siemens per cm, then, depending on the frequency of the voltage applied to the electrodes, the two cell types could each be made to experience either a negative or positive dielectrophoretic force. For example, when a voltage of 20 V p/p sinewave at a frequency of 10 kHz was applied to the electrodes, the dead yeast cells were observed to collect at the outer tips of the electrode castellations (as shown in FIG. 5A) as a result of experiencing a positive dielectrophoretic force, whilst the live yeast cells were directed by a negative dielectrophoretic force into a triangular-shaped aggregation in the regions between the electrode castellations away from the electrode sides, as shown in FIG. 5C. The overall collection of the live and dead yeast cells is similar to that shown in FIG. 6, where the live yeast cells are labelled as particle type 15 and the dead yeast cells are labelled as particle type 16. On the other hand, if a voltage of 20 V p/p sinewave at a frequency of 10 MHz was applied to the electrodes, then the live yeast cells experienced a positive dielectrophoretic force and collected in the form of FIG. 5A, whilst the dead cells experienced a negative dielectrophoretic force and aggregated in the triangular form as shown in FIG. 5B.

EXAMPLE 3

A cell was taken with an array of interdigitated, castellated, electrodes of the same geometry and dimensions as that used in Example 1 above. A suspension in a medium of deionized water was prepared, containing as suspended particles two types of latex particles of diameter 1.27 microns. The first type of latex particle was coated with the antibody raised in rabbit against horseradish peroxidase, whilst the second type of latex particle was coated with horseradish peroxidase-labelled antibody raised in swine against the horseradish peroxidase antibody raised in rabbit. The final suspension of electrical conductivity 4.1 micro-Siemens per cm was formed by mixing together in equal volumes a suspension of latex particle of the first type, of optical density 0.8 at a wavelength of 635 nm at a 1 cm path length, with a suspension of latex particle of the second type of optical density 0.54 at a wavelength of 635 nm at a 1 cm path length.

On application of a voltage of 4 V p/p sinewave at a frequency of 1 kHz to the electrodes, both latex particle types experienced a negative dielectrophoretic force and rapidly aggregated at regions of the upper electrode surfaces, away from the electrode sides, as shown in FIG. 5B. This aggregation brought both types of latex particle into close contact with each other, and greatly accelerated the rate of interaction between the two antibody types coated on the latex particles. On removing the applied voltage to the electrodes, a significant number of the latex particles were observed to be bound together as a result of the dielectrophoretically-induced interaction of the latex particles.

EXAMPLE 4

Figure 7A:
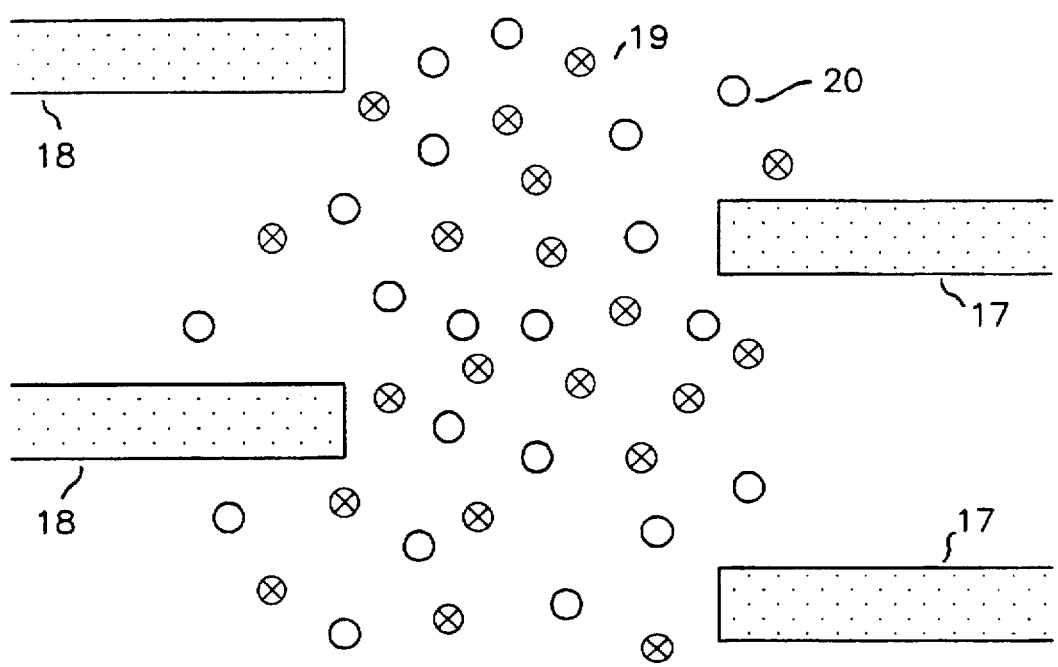
FIG. 7A shows the random distribution of two particle types in the regions near two independent pairs of electrodes.
Figure 7B:
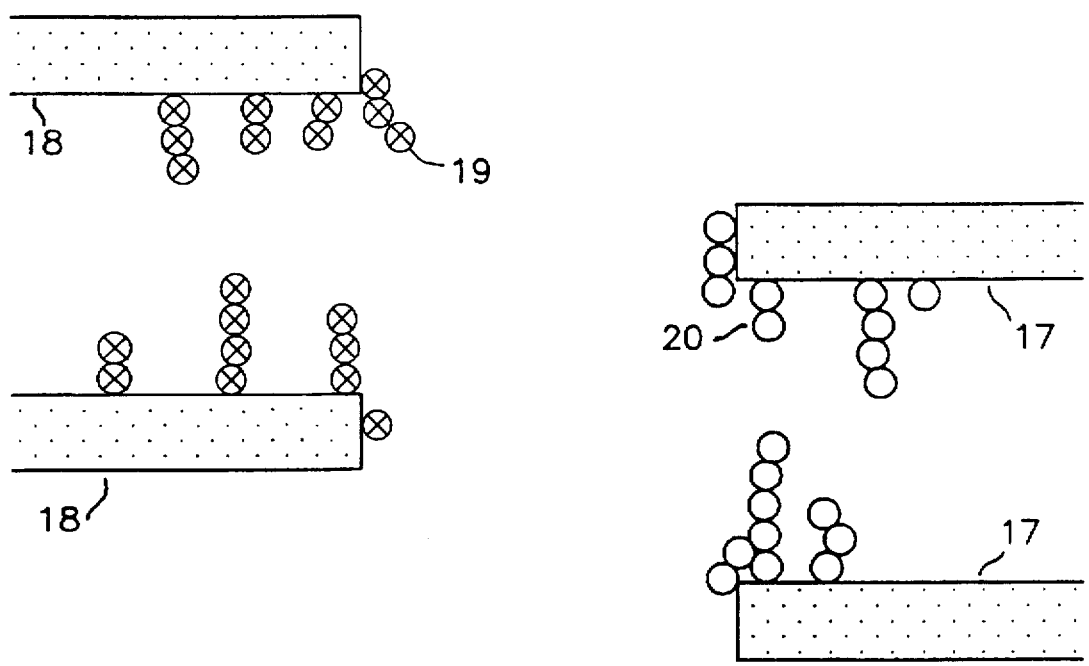
FIG. 7B shows the resulting distribution of two particle types after the independent electrode pairs have been energized by two characteristically different voltages.
Figure 8:
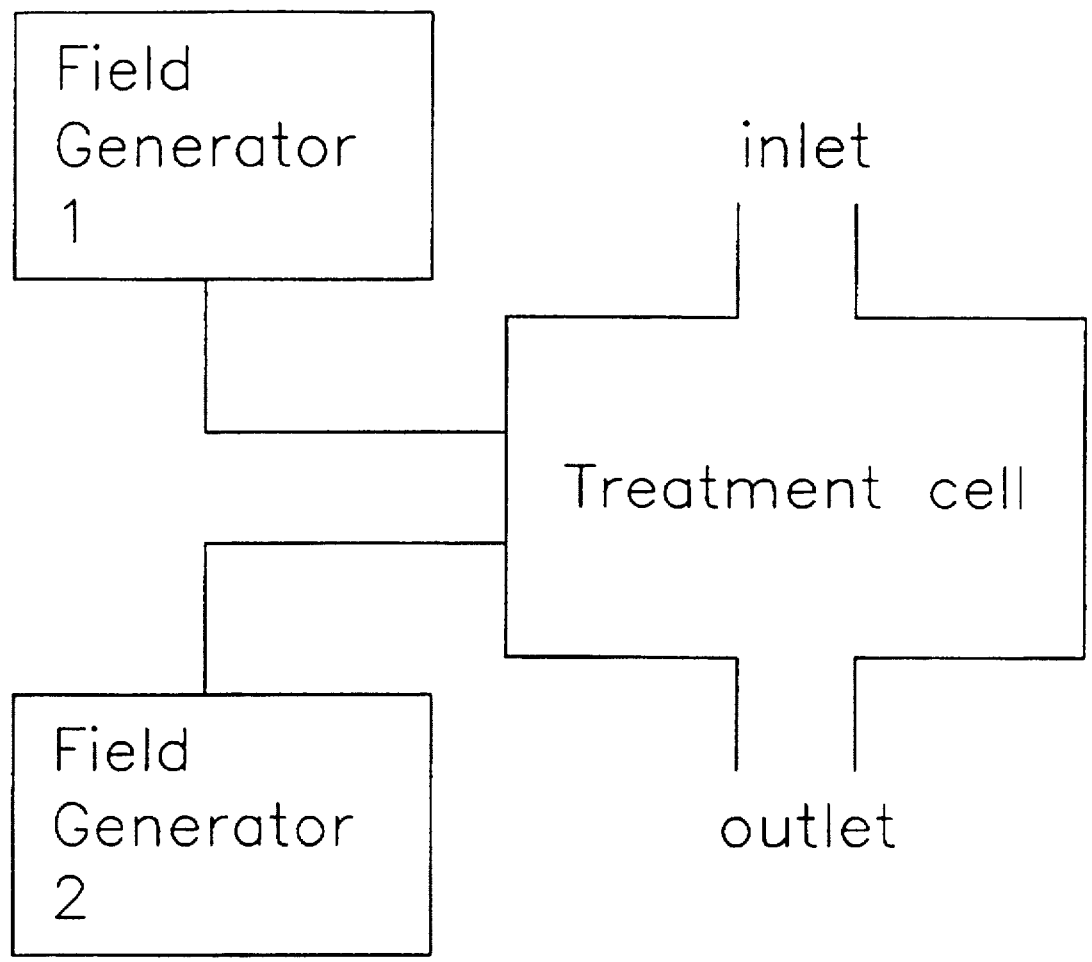
FIG. 8 shows a block diagram of apparatus which can be used to carry out the method of the invention.
Figure 5C:
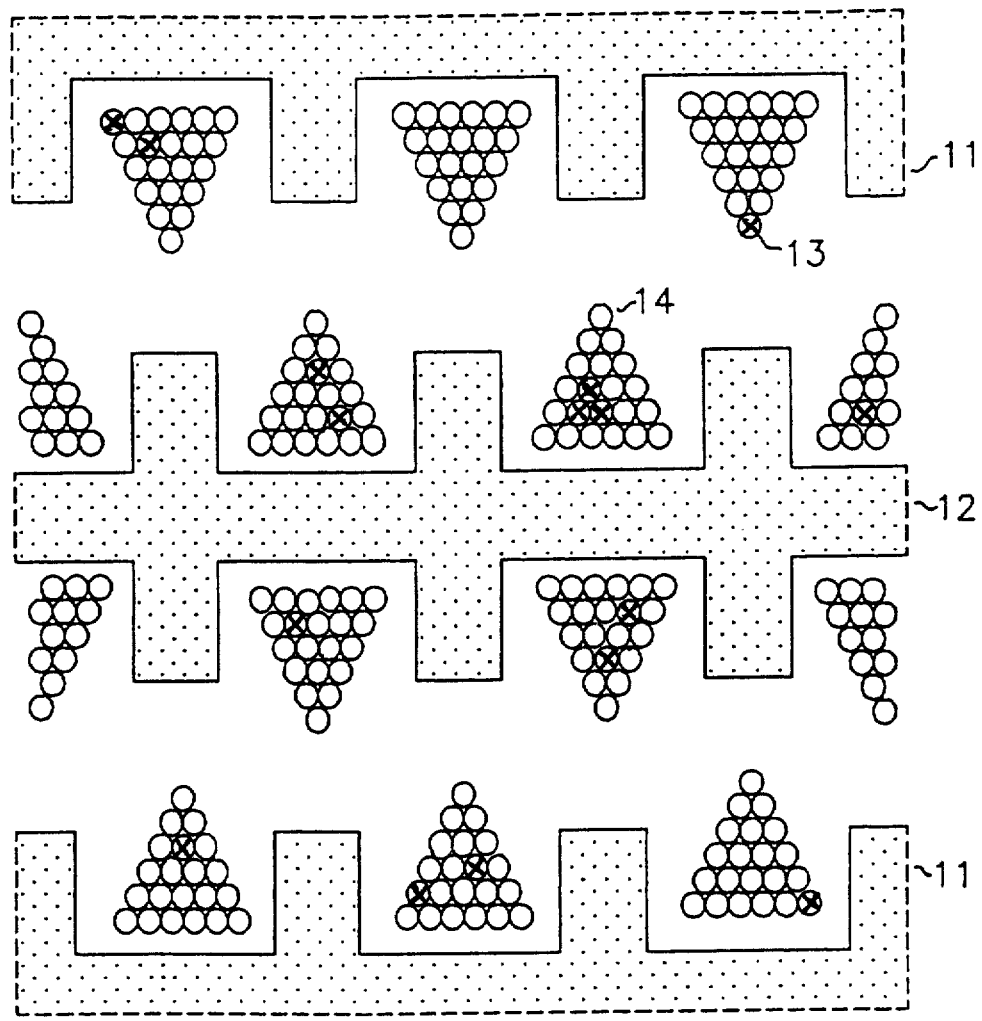

A cell was taken with an electrode geometry similar to that shown in FIGS. 7A and 7B, where the electrode pair 17 can be energized by an applied voltage separately and independently from electrode pair 18. The separation between the two electrodes forming electrode pair 17 was 104 microns, and likewise for the two electrodes forming electrode pair 18. Each electrode element had a width of 32 microns, and a height of 0.1 micron, and the two electrode pairs were spaced 130 microns apart from each other.

A suspension in a medium of 280 mM mannitol in deionized water was prepared, which contained, as suspended particles, equal numbers of live Brewers yeast cells 19 and dead (autoclaved) Brewers yeast cells 20 to an optical absorbance of about 0.8 at a wavelength of 635 nm and a 1 cm optical path length. To this suspension medium was added potassium chloride of sufficient concentration to increase the electrical conductivity of the medium to 150 micro-Siemens per cm. A voltage of 20 V p/p sinewave at a frequency of 10 kHz was applied to electrode pair 17 of FIGS. 7A and 7B, and at the same time a voltage of 20 V p/p sinewave at a frequency of 10 MHz was applied to electrode pair 18. The live Brewers yeast cells 19 were observed to be attracted by a positive dielectrophoretic force towards, and to collect at, the electrode pair 18 energized by the voltage oscillated, and to be repelled by a negative dielectrophoretic force from the regions around the electrode pair 17 energized by the voltage oscillated at 10 kHz. The dead Brewers yeast cells 20, on the other hand, were repelled by a negative dielectrophoretic force from the regions around the electrode pair 18 energized by the voltage oscillated at 10 mHz, but were attracted by a positive dielectrophoretic force towards, and collected at, the electrode pair 17 energized by the voltage oscillated at 10 kHz. The distribution of live 19 and dead Brewers yeast cells 20 before and after application of the 10 kHz and 10 MHz oscillating voltages is shown in FIGS. 7A and 7B, respectively. As can be seen, a spatial separation of the live Brewers yeast cells 19 from the dead Brewers yeast cells 20 is accomplished by this procedure.

EXAMPLE 5

A cell was taken with an array of interdigitated, castellated, electrode pair of the same geometry and dimensions as that used in Example 1 above. Two types of glass beads of nominal diameter 1.0 micron were used. The first type of glass bead was shaken in 5% aminopropyl triethoxysilane in dry acetone for 3 hours, then washed and dried at 70 degrees Centigrade. After drying, the beads were shaken in a 5% solution of nitrophenyl ester of d-biotin in chloroform. This procedure resulted in the first type of glass bead being coated with a film of d-biotin. The second type of glass bead was shaken in a solution containing 1 mg per ml of avidin in phosphate buffered saline at pH 7.7 for 20 minutes. The treated beads were then washed three times in phosphate buffered saline solution. This procedure resulted in the second type of glass bead being coated with a film of avidin. The first and second type 1 and 2 were then separately suspended in a solution of potassium chloride of electrical conductivity 3.5 micro-Siemens per cm.

The final suspension was formed by mixing together in equal volumes a suspension of the first type of glass bead, of optical density 0.8 at a wavelength of 635 nm at 1 cm optical path length, with a suspension of the second type glass bead of optical density 0.8 at a wavelength of 635 nm at a 1 cm optical path length.

On application of a voltage of 6 V p/p sinewave at a frequency of 800 Hz to the electrodes, both glass particle types experienced a negative dielectrophoretic force and aggregated at regions of the upper electrode surfaces, away from the electrode sides, similar to that shown in FIG. 5B. On removal of the applied voltage, a significant number of the glass beads were observed to be firmly bound together as a result of avidin-biotin complexes being formed between the surfaces of both types of glass beads.

What is claimed is:

1. A method of promoting a desired reaction between particles suspended in a liquid, said method comprising steps of:

applying, at a first frequency, a first non-uniform electrical field to a region of said liquid from an electrode array; and applying, at a second frequency, a second non-uniform electrical field to said region of said liquid from said electrode array substantially simultaneously with said application of said first non-uniform electrical field, said second non-uniform field being independent of said first non-uniform electrical field;

said first non-uniform electrical field and said second non-uniform electrical field promoting said desired reaction using dielectrophoretic forces on said particles; and at least one of said first frequency and said second frequency being chosen to effect a negative dielectrophoretic force on only some of said particles suspended in said liquid.

2. A method according to claim 1, further comprising a step of:

modifying at least one of an electrical conductivity and a dielectric constant of at least one of said liquid and said particles to further promote said desired reaction.

3. A method of promoting said desired reaction between said particles suspended in said liquid according to claim 1, wherein:

said electrode array includes parallel electrode pair.

4. A method of promoting said desired reaction between said particles suspended in said liquid according to claim 1, said method comprising further steps of:

determining said first frequency to be a first value which causes a negative dielectrophoretic force on said only some particles suspended in said liquid; and determining said second frequency to be a second value which causes a positive dielectrophoretic force on others of said particles other than said only some particles suspended in said liquid.

5. A method of promoting said desired reaction between said particles suspended in said liquid according to claim 1, said method comprising further steps of:

determining said first frequency to be a first value which causes a negative dielectrophoretic force on said only some particles suspended in said liquid; and determining said second frequency to be a second value which causes a negative dielectrophoretic force on others of said particles other than said only some particles suspended in said liquid.

6. A method of promoting said desired reaction between said particles suspended in said liquid according to claim 1, said method comprising further steps of:

determining said first frequency to be a first value which causes a negative dielectrophoretic force on said only some particles suspended in said liquid; and determining said second frequency to be a second value which causes a further negative dielectrophoretic force on said only some particles suspended in said liquid.

7. A method of promoting said desired reaction between said particles suspended in said liquid according to claim 1, wherein:

said electrode array is interdigitated and creates field traps wherein at least some of said particles suspended in said liquid agglomerate using negative dielectrophoretic forces.

8. A method of promoting said desired reaction between said particles suspended in said liquid according to claim 7, wherein:

said interdigitated electrode array is castellated.

9. A method of promoting said desired reaction between said particles suspended in said liquid according to claim 7, wherein:

said interdigitated electrode array includes a repeating pattern array.

10. A method of promoting said desired reaction between said particles suspended in said liquid according to claim 7, wherein:

said interdigitated electrode array forms an inter-engaged comb-like pattern with an extending portion of a first electrode lying between two oppositely extending and neighboring portions of a second electrode.

11. A method of promoting said desired reaction between said particles suspended in said liquid according to claim 7, wherein:

said electrode array is mounted on an external wall of a treatment cell, said treatment cell including perforations in said external wall to allow removal of particles effected by said desired reaction through said perforations.

12. A method of promoting a desired reaction between particles suspended in a liquid, said method comprising steps of:

applying, at a first frequency, a first non-uniform electrical field to a region of said liquid from an electrode array; and superimposing, at a second frequency, a second non-uniform electrical field to said region of said liquid from said electrode array substantially simultaneously with said application of said first non-uniform electrical field, said second frequency being different from said first frequency, said second non-uniform field being independent of said first non-uniform electrical field;

wherein said first non-uniform electrical field and said second non-uniform electrical field promote said desired reaction using dielectrophoretic forces on said particles.

13. A method of promoting a desired reaction between particles suspended in said liquid, said method comprising steps of:

introducing a volume of said liquid, including said suspended particles, into a treatment cell provided with electrodes;

applying a first electrical signal to said electrodes to generate a redistribution of said particles under an effect of a first dielectrophoretic force;

applying, simultaneously with said first electrical signal, a second electrical signal to said electrodes, a frequency of said second electrical signal being different from a frequency of said first electrical signal, wherein said frequency of said second electrical signal is chosen taking into account a dielectric constant and electrical conductivity of said particles and said liquid to produce a second dielectrophoretic force acting on said particles, said second dielectrophoretic force being different from said first dielectrophoretic force.

14. A method of promoting a desired reaction between particles suspended in said liquid according to claim 13, wherein one of said first electrical signal and said second electrical signal applies a negative dielectrophoretic force on only some of said particles suspended in said liquid.

15. A method of promoting a desired reaction between particles suspended in said liquid according to claim 13, said method further comprising:

modifying one of said electrical conductivity and said dielectric constant of one of said liquid and said particles.

16. A method of promoting a desired reaction between particles suspended in said liquid according to claim 13, said method further comprising:

determining said frequency of said first electrical signal to be a first value which causes a negative dielectrophoretic force on only some of said particles suspended in said liquid; and determining said frequency of said second electrical signal to be a second value which causes a positive dielectrophoretic force on others of said particles other than said only some particles suspended in said liquid.

17. A method of promoting a desired reaction between particles suspended in said liquid according to claim 13, said method further comprising:

determining said frequency of said first electrical signal to be a first value which causes a negative dielectrophoretic force on only some of said particles suspended in said liquid; and determining said frequency of said second electrical signal to be a second value which causes a negative dielectrophoretic force on others of said particles other than said only some particles suspended in said liquid.

18. A method of promoting a desired reaction between particles suspended in said liquid according to claim 13, said method further comprising:

determining said frequency of said first electrical signal to be a first value which causes a negative dielectrophoretic force on only some of said particles suspended in said liquid; and determining said frequency of said second electrical signal to be a second value which causes a further negative dielectrophoretic force on said only some particles suspended in said liquid.

19. A method of promoting a desired reaction between particles suspended in a liquid, said particles including first particles and second particles, said method comprising steps of:

introducing a volume of said liquid, including said suspended particles, into a treatment cell provided with electrodes;

applying, at a first frequency, a first electrical signal to said electrodes to generate a redistribution of positions of said particles under an effect of a first dielectrophoretic force;

applying, at a second frequency different from said first frequency, while said particles occupy said redistribution of positions, a second electrical signal to said electrodes, said second frequency being chosen taking into account a dielectric constant and electrical conductivity of said particles and said liquid to produce a second dielectrophoretic force acting on said particles, one of said first and second electrical signals acting to apply a negative dielectrophoretic force on only said first particles, and the other of said first and second electrical signals acting to apply only one of a negative dielectrophoretic force and a positive dielectrophoretic force on both said first particles and said second particles.

20. A method of promoting a desired reaction between particles suspended in said liquid according to claim 19, said method further comprising:

modifying one of said electrical conductivity and said dielectric constant of one of said liquid and said particles.

21. A method of promoting a desired reaction between particles suspended in a liquid, said particles including first particles and second particles, said method comprising steps of:

introducing a volume of said liquid, including said suspended particles, into a treatment cell provided with electrodes;

applying, at a first frequency, a first electrical signal to said electrodes to generate a redistribution of positions of said particles under an effect of a first dielectrophoretic force acting on said first particles and said second particles, said first dielectrophoretic force being one of a positive dielectrophoretic force and a negative dielectrophoretic force;

applying, at a second frequency different from said first frequency, while said particles occupy said redistribution of positions, a second electrical signal to said electrodes, said second frequency being chosen taking into account a dielectric constant and electrical conductivity of said particles and said liquid to produce a second dielectrophoretic force acting on said particles, said second dielectrophoretic force being a positive dielectrophoretic force acting on one of said first particles and said second particles, and said second dielectrophoretic force being a negative dielectrophoretic force acting on the other of said first particles and said second particles.

22. A method of promoting a desired reaction between particles suspended in said liquid according to claim 21, said method further comprising:

modifying one of said electrical conductivity and said dielectric constant of one of said liquid and said particles.

* * * * *

UNITED STATES PATENT AND TRADEMARK OFFICE
CERTIFICATE OF CORRECTION

PATENT NO.      : 5,795,457
DATED           : Aug. 18, 1998
INVENTOR(s)     : PETHIG et al.

It is certified that error appears in the above-identified patent and that said Letters Patent is hereby corrected as shown below:

Please read Fig. 5C as shown on the herewith corrected copy in which X is added in the circles that were originally black.

Signed and Sealed this

Twenty-ninth Day of May, 2001

*Attest:*

NICHOLAS P. GODICI

*Attesting Officer*    *Acting Director of the United States Patent and Trademark Office*